United States Patent [19]

Grasselli et al.

[11] 4,324,908

[45] Apr. 13, 1982

[54] PREPARATION OF UNSATURATED ACIDS AND ESTERS FROM SATURATED CARBOXYLIC ACID DERIVATIVES AND CARBONYL COMPOUNDS OVER PHOSPHATE CATALYSTS

[75] Inventors: Robert K. Grasselli, Chagrin Falls; Andrew T. Guttmann, Maple Heights, both of Ohio

[73] Assignee: Standard Oil Company, Cleveland, Ohio

[21] Appl. No.: 221,583

[22] Filed: Dec. 31, 1980

[51] Int. Cl.³ ............................................ C07C 67/343
[52] U.S. Cl. ................................... 560/210; 252/435; 252/437
[58] Field of Search .................... 560/210, 211, 212; 562/599

[56] References Cited

U.S. PATENT DOCUMENTS

| | | | |
|---|---|---|---|
| 2,485,510 | 10/1949 | Redman | 562/599 |
| 3,014,958 | 12/1961 | Koch et al. | 560/210 |
| 3,912,772 | 10/1975 | Pfeffer et al. | 562/599 |

*Primary Examiner*—Natalie Trousof
*Assistant Examiner*—L. Hendriksen
*Attorney, Agent, or Firm*—David J. Untener; Larry W. Evans; Herbert D. Knudsen

[57] ABSTRACT

Promoted phosphate catalysts have been found to be effective for the vapor phase condensation of saturated monocarboxylic acids or esters with formaldehyde, to produce unsaturated carboxylic acids or esters.

23 Claims, No Drawings

PREPARATION OF UNSATURATED ACIDS AND ESTERS FROM SATURATED CARBOXYLIC ACID DERIVATIVES AND CARBONYL COMPOUNDS OVER PHOSPHATE CATALYSTS

BACKGROUND OF THE INVENTION

The condensation reaction of saturated carboxylic acids and esters with carbonyl compounds to produce unsaturated acids and esters is known in the art. U.S. Pat. No. 2,734,074 discloses that formaldehyde reacts with lower alkyl esters of aliphatic monocarboxylic acid to produce lower alkyl esters of alpha-beta unsaturated acids in the presence of a dehydration catalyst. Suitable catalysts found in this reference are lead chromate on silica gel, zinc chromite on silica gel, vanadia on alumina, zirconia on silica gel, or lead sulfate on silica gel.

U.S. Pat. No. 3,014,958 discloses an improvement upon this reaction by having present, in the reaction mixture, a substantial concentration of the desired unsaturated ester, generally exceeding about 7% of the weight of reactant ester. The reaction is again performed in the presence of a dehydration catalyst, suitable catalysts being phosphates of alkali and alkaline earths, aluminum and boron. Additionally, oxides, including mixed oxides of 20 additional metals are disclosed such as zinc, vanadium, chromium, molybdenum, tungsten, etc.

U.S. Pat. No. 4,165,438 discloses that acrylic acids and esters are produced by reacting a lower alkanoic acid or lower alkyl ester with formaldehyde in the presence of a vanadium orthophosphate catalyst having a specific surface area. For comparison purposes, this reference discloses inferior phosphate catalysts of lithium, sodium, magnesium, zinc, aluminum, chromium, cerium, niobium, antimony and bismuth.

Other catalysts useful in this reaction have been supported rare earth metal oxides disclosed in U.S. Pat. No. 3,701,798; X or Y zeolites with cesium, rubidium or potassium cations as found in U.S. Pat. No. 4,115,424; pyrogenic silica promoted with Groups IIA and IIIA metals disclosed in U.S. Pat. No. 3,933,888; and phosphates of magnesium, calcium, aluminum, zirconium, thorium or titanium as found in German Pat. No. 2,615,887.

SUMMARY OF THE INVENTION

The invention may be stated as a process for producing unsaturated carboxylic acids and esters which comprises passing into a reaction zone, a mixture of a saturated monocarboxylic acid or its ester with formaldehyde or a formaldehyde derivative, in the presence of a catalyst having the empirical formula $$A_aPO_x$$

wherein
A is Fe, Ni, Co, Mn, Cu, Ag or mixtures thereof;
a is 0.2–3.0; and
x is determined by the nature and oxidation state of the other elements.

More specifically, the catalyst of the present invention may be promoted by various elements, thus having the empirical formula $$A_aB_bC_cPO_x$$

wherein
A is Fe, Ni, Co, Mn, Cu, Ag or mixtures thereof;
B is alkali metal, alkaline earth metal, Tl or mixtures thereof;
C is Se, Y, La, rare earth metal, Th, Nb, Mo, Te, Cr, Ta, U or mixtures thereof; and
a=0.2–3.0;
b=0–1.5;
c=0–2.0; and
x is determined by the nature and oxidation state of the other elements.

The preferred values of a, b, and c should be such that the value of $(an_a+bn_b+cn_c)$ is greater than or equal to 1.0, and less than or equal to 5, where $n_a$ is the valence of the ions from Group A, $n_b$ is the valence of the ions from Group B, and $n_c$ is the valence of the ions from Group C.

As noted in the Background, the condensation reaction itself is knwon in the art and may be expressed by the following equation using methyl acetate as an example:

$$H_2CO + H_3C-COOCH_3$$
$$H_2C=CH-COOCH_3 + H_2O$$

It is conveniently carried out by mixing formaldehyde in a suitable form with the appropriate acid or ester, e.g. methyl acetate in the desired ratio, vaporizing the mixture, and passing the vapors continuously over the catalyst. Fixed or fluid bed operation is possible. Steam or inert diluents may be added (e.g. $N_2$). Commercial aqueous or alcoholic $CH_2O$ solutions, formals such as methylal, or volatile $(CH_2O)_x$ compounds, such as s-trioxane, may serve as a formaldehyde source. Alternately, the gaseous product effluent from a formaldehyde manufacturing process unit (e.g. by methanol oxidation) may be passed over a catalyst of this invention, along with the vapors of the appropriate ester or acid.

Preferably, formaldehyde, including formaldehyde derivatives, polymers, oligomers, and precursors thereof are condensed with acetic acid or acetates, or with propionic acid or propionates. A preferred aspect of the invention is to prepare acrylic acid and methacrylic acid derivatives from formaldehyde and acetic/propionic acid and their esters.

The reaction temperature may range from 200 to about 450° C., preferably from 300°–350° C. The average residence time may be from about 2 to about 30 seconds, preferably from 3 to 15 seconds. The molar ratio of acid or esters to formaldehyde may range from 0.1 to about 10.

The catalysts may be used unsupported, but the use of a suitable carrier, such as silica, alumina, mixtures of silica and alumina, amorphous silica-alumina, crystalline aluminosilicates, titania, natural clays and such is preferred. Especially good results are obtained with alumina as support. The concentration of the active catalyst on the support may range from about 10 to about 80% by weight.

The catalysts are prepared by methods known in the art. Thus, e.g. compounds of the various metals from the Groups A, B and C such as oxides, hydroxides, carbonates, nitrates or acetates may be mixed with an aqueous solution of phosphoric acid to form a slurry which is then heated and evaporated to dryness. The support may be introduced at the various stages of the slurry preparation. The order of adding the various constituents of the slurry may vary. Instead of phosphoric acid, other phosphorus compounds, e.g., ammonium phosphates, $P_2O_5$, polyphosphoric acid or mixtures thereof, can be used. The dried slurry may be heat treated at temperatures above 200° C. to decompose ammonium salts and anions such as nitrate or acetate; the catalyst is then subjected to a final calcination at temperatures from about 300° to about 650° C., preferably from 350° to 550° C.

REACTION OF METHYL ACETATE WITH METHYLAL OVER FE-P CATALYSTS

Examples 1–10

A catalyst having the composition 50% $K_{0.4}Th_{0.09}Fe_{0.45}PO_x + 50\%$ $Al_2O_3$ was prepared as follows. A slurry of 44.1 g hydrated alumina (Catapal SB, 85% $Al_2O_3$,) in 170 ml $H_2O$ was heated to 70° C. and a solution of 33.2 g $(NH_4)_2HPO_4$ in 60 ml $H_2O$ was added with stirring, followed by the addition of a solution of 12.4 g Th $(NO_3)_4.4H_2O$ and 45.4 g Fe $(NO_3)_3.9H_2O$ in 40 ml $H_2O$, and a solution of 10.2 g $KNO_3$ in 20 ml $H_2O$. The heavy slurry was evaporated to a low volume at about 90° C., then dried at 120°–125° C. The dry material was treated 3 hours at 290° C., 3 hours at 350° C., ground and screened to 20/35 mesh size, and finally calcined 5 hours at 500° C. Five cc of the catalyst was charged to a fixed-bed microreactor equipped with a preheat leg serving as a vaporizer, and immersed in a temperature-controlled salt bath at 330° C. Liquid feed consisting of a mixture of methylacetate and methylal (formaldehyde dimethylacetal) in a molar ratio of 10:1 was injected by a syringe pump into the reactor, through the preheat leg, over a period of 70 minutes, at such a rate that the feed vapors passed over the catalyst at an average contact time of 10 seconds. The reactor effluent was condensed, weighed and analyzed by gas chromatography. In the same manner as the catalyst of Example 1, catalysts having the promoters shown in Table I were prepared. Table I shows the results of Examples 1–10 with the percent per pass conversion (PPC) being based on methylal. In Example 10 nitrogen was added as diluent, and the average contact time was 4 seconds.

REACTION OF METHYLPROPIONATE WITH METHYLAL OVER PHOSPHATE CATALYSTS

Examples 11–18

Iron-phosphate catalysts containing various promoters were prepared in the manner of Example 1. The catalysts of Examples 11 and 16 were supported on 50% $SiO_2$, whereas those of Examples 12–15, 17, and 18 were supported in the manner of Example 1 on 50% $Al_2O_3$.

5 cc of the catalyst was charged to the reactor of Example 1. A feed ratio of methyl propionate/methylal of 10/1 was passed over the catalyst at a contact time of ten seconds for a period of sixty minutes. The reaction temperature is as shown in Table II. The per pass conversion to products shown in Table II are based on methylal. In Examples 17 and 18 nitrogen was added as diluent, and the average contact time was 4 seconds.

REACTION OF METHYL ACETATE WITH METHYLAL OVER MIXED PHOSPHATE CATALYSTS

Examples 19–26

In the same manner of Example 1, mixed phosphate catalysts having the composition shown in Table III were prepared being supported on 50% $Al_2O_3$. All catalysts were calcined at a temperature of 500° C.

A feed of methyl acetate/methylal in a ratio of 10/1 was passed over the catalyst with a contact time of ten seconds, a reaction temperature of 330° C., and a time on stream of 70 minutes. The results, with the per pass conversion based on methylal are presented in Table III.

REACTION OF ACETIC ACID WITH FORMALDEHYDE

Example 27

A catalyst having the composition $Th_{0.11}Fe_{0.54}PO_x$ having a support of 50% $Al_2O_3$ and being calcined at 500° C. was used in the reaction of acetic acid with formaldehyde. Acetic acid/formaldehyde in a ratio of 10/1 was passed over the catalyst at a reaction temperature of 330° C. in a contact time of 10 seconds. Five parts steam was additionally added to the feed. The per pass conversion based on methylal was 29.7% to acrylic acid.

TABLE I

Reaction of Methyl Acetate with Methylal Over Phosphate Catalysts

| Example | Catalyst | % Conver. Methylal | % PPC Methyl Acrylate | % PPC Acrylic Acid | Total |
|---|---|---|---|---|---|
| 1 | $K_{0.4}Th_{0.09}Fe_{0.45}PO_x$ | 99 | 57.3 | 2.4 | 59.7 |
| 2 | $K_{0.4}Fe_{0.57}PO_x$ | 99.1 | 44.9 | 2.5 | 47.4 |
| 3 | $Th_{0.17}Fe_{0.87}PO_x$ | 99.7 | 27.5 | 2.3 | 29.8 |
| 4 | $K_{0.4}Th_{0.4}Fe_{0.43}PO_x$ | 100 | 48.1 | 1.2 | 49.3 |
| 5 | $K_{0.4}Th_{0.24}Fe_{0.24}PO_x$ | 98.8 | 54.1 | 2.5 | 56.6 |
| 6 | $La_{0.53}Fe_{0.57}PO_x$ | 99.6 | 35.7 | 2.1 | 37.8 |
| 7 | $K_{0.4}La_{0.28}Fe_{0.28}PO_x$ | 100 | 56.5 | 2.1 | 58.6 |
| 8 | $Ce_{0.53}Fe_{0.57}PO_x$ | 99.6 | 35.0 | 2.6 | 37.6 |
| 9 | $K_{0.4}Ce_{0.28}Fe_{0.28}PO_x$ | 100 | 50.0 | 1.6 | 51.6 |
| 10 | $K_{0.4}Cr_{0.1}Fe_{0.47}Mo_{0.1}PO_x$ | 100 | 40.7 | 2.9 | 43.6 |

TABLE II

REACTION OF METHYL PROPIONATE WITH METHYLAL OVER PHOSPHATE CATALYSTS

| Example | Catalyst | Reaction Temp. | % Conv. Methylal | % PPC Methyl Methacrylate | % PPC Methacrylic Acid | Total |
|---|---|---|---|---|---|---|
| 11 | $Cs_{0.4}Fe_{0.5}Cr_{0.4}PO_x$ | 375 | 94.6 | 27.0 | 0.3 | 27.3 |
| 12 | $Cs_{0.4}Fe_{0.5}Cr_{0.47}PO_x$ | 375 | 76.3 | 39.2 | 0.8 | 40.0 |
| 13 | $Tl_{0.4}Fe_{0.5}Cr_{0.47}PO_x$ | 375 | 98.5 | 39.8 | 1.5 | 41.3 |
| 14 | $K_{0.4}Fe_{0.5}Ce_{0.47}PO_x$ | 350 | 93.2 | 49.3 | 0.7 | 50.0 |
| 15 | $K_{0.4}Fe_{0.6}Cu_{0.56}PO_x$ | 330 | 97.1 | 42.6 | 3.3 | 45.9 |
| 16 | $Cs_{0.4}Fe_{0.97}PO_x$ | 375 | 44.4 | 8.2 | 0 | 8.2 |
| 17 | $K_{0.4}Cr_{0.1}Fe_{0.47}Mo_{0.1}PO_x$ | 350 | 98.0 | 47.9 | 1.8 | 49.7 |
| 18 | $K_{0.4}Mn_{0.15}Fe_{0.5}Mo_{0.1}PO_x$ | 350 | 97.6 | 48.2 | 4.7 | 52.9 |

TABLE III

Reaction of Methyl Acetate with Methylal Over Phosphate Catalysts

| Example | Catalyst | % Conv. Methylal | % PPC Methyl Acrylate | % PPC Acrylic Acid | % PPC Total |
|---|---|---|---|---|---|
| 19 | $K_{0.4}Th_{0.48}Co_{0.48}PO_x$ | 100 | 45.4 | 1.0 | 46.4 |
| 20 | $K_{0.4}Th_{0.58}Ag_{0.58}PO_x$ | 96.3 | 60.4 | 3.0 | 63.3 |
| 21 | $K_{0.4}Cu_{1.45}PO_x$ | 99.4 | 31.8 | 0 | 31.8 |
| 22 | $K_{0.4}Th_{0.48}Cu_{0.48}PO_x$ | 98.6 | 68.5 | 10.1 | 78.5 |
| 23 | $K_{0.4}Th_{0.48}Cu_{0.48}Te_{0.1}PO_x$ | 100 | 42.3 | 4.6 | 46.9 |
| 24 | $K_{0.4}La_{0.58}Cu_{0.58}PO_x$ | 98.5 | 78.4 | 2.0 | 80.4 |
| 25 | $K_{0.4}Cr_{0.58}Cu_{0.58}PO_x$ | 98.9 | 46.0 | 5.0 | 51.0 |
| 26 | $K_{0.4}Ni_{0.725}Cu_{0.725}PO_x$ | 100 | 19.7 | 1.5 | 21.2 |

We claim:

1. A process for producing unsaturated carboxylic acid and esters which comprises passing into a reaction zone, a vaporous mixture of a saturated monocarboyxlic acid or its ester with formaldehyde or a formaldehyde derivative, at a temperature of from 200° C. to about 450° C., in the presence of a catalyst having the empirical formula $$A_aPO_x$$

wherein

A is Fe, Ni, Co, Mn, Cu, Ag or mixtures thereof;
a is 0.2–3.0; and
x is determined by the nature and oxidation state of the other elements.

2. The process of claim 1 wherein the catalyst is on a support comprising alumina.

3. A process for producing unsaturated carboxylic acid and esters which comprises passing into a reaction zone, a vaporous mixture of a saturated monocarboxylic acid or its ester with formaldehyde or a formaldehyde derivative, at a temperature of from 200° C. to about 450° C., in the presence of a catalyst having the empirical formula $$A_aB_bC_cPO_x$$

wherein

A is Fe, Ni, Co, Mn, Cu, Ag or mixtures thereof;
B is alkali metal, alkaline earth metal, TL or mixtures thereof;
C is Se, Y, La, rare earth metal, Th, Nb, Mo, Te, Cr, Ta, U or mixtures thereof; and
A=0.2–3.0;
b=0–1.5;
c=0–2.0; and
x is determined by the nature and oxidation state of the other elements.

4. The process of claims 1 or 3 wherein the formaldehyde derivative is methylal.

5. The process of claims 1 or 3 wherein the formaldehyde derivative is trioxane.

6. The process of claims 1 or 3 wherein the saturated monocarboxylic acid is acetic acid.

7. The processes of claims 1 or 3 wherein the saturated monocarboxylic acid is propionic acid.

8. The process of claims 1 or 3 wherein the ester fed to the reaction zone is methylacetate.

9. The process of claims 1 or 3 wherein the ester fed to the reaction zone is methylpropionate.

10. The process of claim 3 wherein A is iron.

11. The process of claim 10 wherein B is an alkali metal.

12. The process of claim 11 wherein B is potassium.

13. The process of claims 10 or 11 wherein C is thorium.

14. The process of claim 10 wherein C is lanthanum.

15. The process of claim 10 wherein C is chromium.

16. The process of claim 3 wherein A is iron and copper.

17. The process of claim 3 wherein A is cobalt.

18. The process of claim 3 wherein A is silver.

19. The process of claim 3 wherein A is copper.

20. The process of claims 17, 18 or 19 wherein B is an alkali metal.

21. The process of claims 17, 18 or 19 wherein C is thorium.

22. The process of claim 3 wherein the catalyst is on a support comprising alumina.

23. The process of claim 10 or 11 wherein C is one or more elements selected from the group of Cr, La, Ce, Th, and Mo.

* * * * *